United States Patent
Kajino et al.

(10) Patent No.: US 10,615,328 B2
(45) Date of Patent: Apr. 7, 2020

(54) PIEZOELECTRIC ACTUATOR, PIEZOELECTRIC MOTOR, ROBOT, HAND, AND PUMP

(71) Applicant: Seiko Epson Corporation, Tokyo (JP)

(72) Inventors: Kiichi Kajino, Matsumoto (JP); Yutaka Arakawa, Hara (JP)

(73) Assignee: Seiko Epson Corporation (JP)

( * ) Notice: Subject to any disclaimer, the term of this patent is extended or adjusted under 35 U.S.C. 154(b) by 560 days.

(21) Appl. No.: 15/469,969

(22) Filed: Mar. 27, 2017

(65) Prior Publication Data

US 2017/0279033 A1    Sep. 28, 2017

(30) Foreign Application Priority Data

Mar. 28, 2016    (JP) .................. 2016-063903

(51) Int. Cl.
| | |
|---|---|
| H01L 41/107 | (2006.01) |
| H01L 41/09 | (2006.01) |
| A61B 34/30 | (2016.01) |
| A61B 34/00 | (2016.01) |
| A61M 5/142 | (2006.01) |
| F04B 43/08 | (2006.01) |
| F04B 43/09 | (2006.01) |
| F04B 43/12 | (2006.01) |
| H02N 2/00 | (2006.01) |
| H02N 2/10 | (2006.01) |

(Continued)

(52) U.S. Cl.
CPC .............. *H01L 41/09* (2013.01); *A61B 34/30* (2016.02); *A61B 34/70* (2016.02); *A61M 5/142* (2013.01); *F04B 43/082* (2013.01); *F04B 43/095* (2013.01); *F04B 43/1223* (2013.01); *H02N 2/004* (2013.01); *H02N 2/0075* (2013.01); *H02N 2/103* (2013.01); *B25J 9/12* (2013.01); *B25J 15/02* (2013.01)

(58) Field of Classification Search
CPC ......... H01L 41/09; A61B 34/30; A61B 34/70; A61M 5/142; F04B 43/082; F04B 43/095; G04B 43/1223; H02N 2/004; H02N 2/0075; H02N 2/103; B25J 9/12; B25J 15/02
USPC ...................... 310/316.01–316.03, 318, 319
See application file for complete search history.

(56) References Cited

U.S. PATENT DOCUMENTS

| | | |
|---|---|---|
| 2004/0212278 A1 | 10/2004 | Miyazawa |
| 2008/0078262 A1 | 4/2008 | Murata et al. |

FOREIGN PATENT DOCUMENTS

| | | |
|---|---|---|
| EP | 1936707 A2 | 6/2008 |
| JP | 63-171174 A | 7/1988 |
| JP | 11-018456 A | 1/1999 |

(Continued)

OTHER PUBLICATIONS

Extended European Search Report for Patent Application No. EP17162764.9 dated Aug. 3, 2017 (7 pages).

*Primary Examiner* — Thomas M Dougherty
(74) *Attorney, Agent, or Firm* — Harness, Dickey & Pierce, P.L.C.

(57) ABSTRACT

A piezoelectric actuator includes a first piezoelectric element that outputs a first signal when being driven, a second piezoelectric element that outputs a second signal when being driven, a signal combining part that delays phase of the second signal and outputs a composite signal by combination of the second signal and the first signal, and a drive state determination part that determines respective drive states of the first piezoelectric element and the second piezoelectric element based on the composite signal.

19 Claims, 12 Drawing Sheets

(51) Int. Cl.
*B25J 9/12* (2006.01)
*B25J 15/02* (2006.01)

(56) References Cited

FOREIGN PATENT DOCUMENTS

| | | |
|---|---|---|
| JP | 2006-340528 A | 12/2006 |
| JP | 2008-076696 A | 4/2008 |
| JP | 2008-199774 A | 8/2008 |
| JP | 2015-103619 A | 6/2015 |
| JP | 2015-115542 A | 6/2015 |

PIEZOELECTRIC ACTUATOR, PIEZOELECTRIC MOTOR, ROBOT, HAND, AND PUMP

BACKGROUND

1. Technical Field

The present invention relates to a piezoelectric actuator, piezoelectric motor, robot, hand, and pump.

2. Related Art

An piezoelectric actuator including a piezoelectric element for determination of a drive state of the piezoelectric element based on electric charge (detection signal) generated by the piezoelectric effect with driving of the piezoelectric element is known (e.g. see Patent Document 1 (JP-A-2008-199774)).

For example, an apparatus described in Patent Document 1 has state determination means for determining a state of a piezoelectric element based on a potential difference between both ends of a detection resistance provided in an electric circuit between the piezoelectric element and a ground point.

In the apparatus described in Patent Document 1, a circuit forming the state determination means is necessary with respect to each piezoelectric element, and, when a plurality of piezoelectric elements are used, there is a problem that downsizing is harder because a plurality of the circuits forming the state determination means are necessary and wiring connected to the state determination means is complex.

SUMMARY

An advantage of some aspects of the invention is to provide a piezoelectric actuator that may individually determine respective drive states of a plurality of piezoelectric elements with simplified wiring, and provide a piezoelectric motor, robot, hand, and pump including the piezoelectric actuator.

The advantage can be achieved by the following configurations.

A piezoelectric actuator according to an aspect of the invention includes a first piezoelectric element that outputs a first signal when being driven, a second piezoelectric element that outputs a second signal when being driven, a signal combining part that outputs a composite signal by combination of the second signal with a phase delay and the first signal, and a drive state determination part that determines respective drive states of the first piezoelectric element and the second piezoelectric element based on the composite signal.

According to the piezoelectric actuator, the phase of the second signal is delayed and the composite signal by combination of the first signal and the second signal is used, and thereby, even when the first piezoelectric element and the second piezoelectric element are driven at the same frequency as each other, in the drive state determination part, changes of the drive states of the first piezoelectric element and the second piezoelectric element can be individually detected based on changes in waveform of the composite signal. Accordingly, even if the respective first signal and second signal are not input to the drive state determination part individually, the drive state determination part can individually determine the respective drive states of the first piezoelectric element and the second piezoelectric element based on the composite signal. Further, wires from the first piezoelectric element and the second piezoelectric element can be integrally connected to the drive state determination part. Accordingly, the wires connected to the drive state determination part can be simplified.

In the piezoelectric actuator according to the aspect of the invention, it is preferable that the signal combining part has a plurality of delay circuits having equal amounts of delay to one another.

With this configuration, in the case where the number of piezoelectric elements is equal to or larger than three, the composite signal of the signals from the plurality of piezoelectric elements at equal phase shift intervals or in phase can be obtained.

In the piezoelectric actuator according to the aspect of the invention, it is preferable that n (n is an integer equal to or larger than two) piezoelectric elements including the first piezoelectric element and the second piezoelectric element are provided, and the signal combining part has (n−1) delay circuits having amounts of delay of $2\pi/n$.

With this configuration, the composite signal of the signals from the plurality of piezoelectric elements at equal phase shift intervals can be obtained. When part of the plurality of piezoelectric elements fail, the waveform of the composite signal changes according to the failed parts. Therefore, the failed piezoelectric elements can be specified based on the change in waveform.

In the piezoelectric actuator according to the aspect of the invention, it is preferable that an amplitude detection part that detects an amplitude of the composite signal is provided, and the signal combining part has a delay circuit having an amount of delay of $2\pi$, and the drive state determination part determines the drive states of the first piezoelectric element and the second piezoelectric element based on a detection result of the amplitude detection part.

With this configuration, the composite signal of the first signal and the second signal in phase (the composite signal of the signals from the plurality of piezoelectric elements in phase) can be obtained. When at least one of the first piezoelectric element and the second piezoelectric element fails, the amplitude of the composite signal changes according to the number of fails. Therefore, the presence or absence and the number of the failed piezoelectric elements can be detected based on the change in amplitude, i.e., the detection result of the amplitude detection part.

In the piezoelectric actuator according to the aspect of the invention, it is preferable that a drive signal changing part that changes the drive signals input to the first piezoelectric element and the second piezoelectric element based on the detection result of the amplitude detection part is provided.

With this configuration, the failed piezoelectric elements can be specified based on the composite signal by the change of the drive signals.

In the piezoelectric actuator according to the aspect of the invention, it is preferable that the drive signal changing part changes frequencies of the drive signals.

With this configuration, the composite signal of the signals from the plurality of piezoelectric elements at equal phase shift intervals can be obtained by the change of the frequencies of the drive signals. Therefore, the frequencies of the drive signals are changed after the presence or absence and the number of the failed piezoelectric elements are detected based on the detection result of the amplitude detection part, and thereby, the failed piezoelectric elements can be specified based on the composite signal.

In the piezoelectric actuator according to the aspect of the invention, it is preferable that the drive signal changing part changes waveforms of the drive signals.

With this configuration, the signals from the piezoelectric elements except the failed piezoelectric elements change by the change of the waveforms of the drive signals. In the composite signal, the changes appear with shifts of the amounts of delay of the delay circuits with respect to each of the piezoelectric elements. Therefore, the waveforms of the drive signals are changed after the presence or absence and the number of the failed piezoelectric elements are detected based on the detection result of the amplitude detection part, and thereby, the failed piezoelectric elements can be specified based on the composite signal (more specifically, the delay time of the waveform change appearing in the composite signal).

In the piezoelectric actuator according to the aspect of the invention, it is preferable that the first piezoelectric element and the second piezoelectric element are stacked.

With this configuration, a large drive force can be transmitted to one part of a driven part. Further, even when part of the piezoelectric elements fail, the failed piezoelectric elements can be driven with driving of the rest of the piezoelectric elements.

A piezoelectric motor according to an aspect of the invention includes the piezoelectric actuator according to the aspect of the invention.

According to the piezoelectric motor, the failed piezoelectric element of the plurality of piezoelectric elements of the piezoelectric actuator can be specified with simplified wiring of the piezoelectric actuator.

A robot according to an aspect of the invention includes the piezoelectric actuator according to the aspect of the invention.

According to the robot, the failed piezoelectric element of the plurality of piezoelectric elements of the piezoelectric actuator can be specified with simplified wiring of the piezoelectric actuator.

A hand according to an aspect of the invention includes the piezoelectric actuator according to the aspect of the invention.

According to the hand, the failed piezoelectric element of the plurality of piezoelectric elements of the piezoelectric actuator can be specified with simplified wiring of the piezoelectric actuator.

A pump according to an aspect of the invention includes the piezoelectric actuator according to the aspect of the invention.

According to the pump, the failed piezoelectric element of the plurality of piezoelectric elements of the piezoelectric actuator can be specified with simplified wiring of the piezoelectric actuator.

BRIEF DESCRIPTION OF THE DRAWINGS

The invention will be described with reference to the accompanying drawings, wherein like numbers reference like elements.

DESCRIPTION OF EXEMPLARY EMBODIMENTS

As below, a piezoelectric actuator, piezoelectric motor, robot, hand, and pump according to the invention will be explained in detail based on embodiments shown in the accompanying drawings.

1. Piezoelectric Actuator

First, an embodiment of a piezoelectric actuator according to the invention will be explained.

First Embodiment

Figure 1:
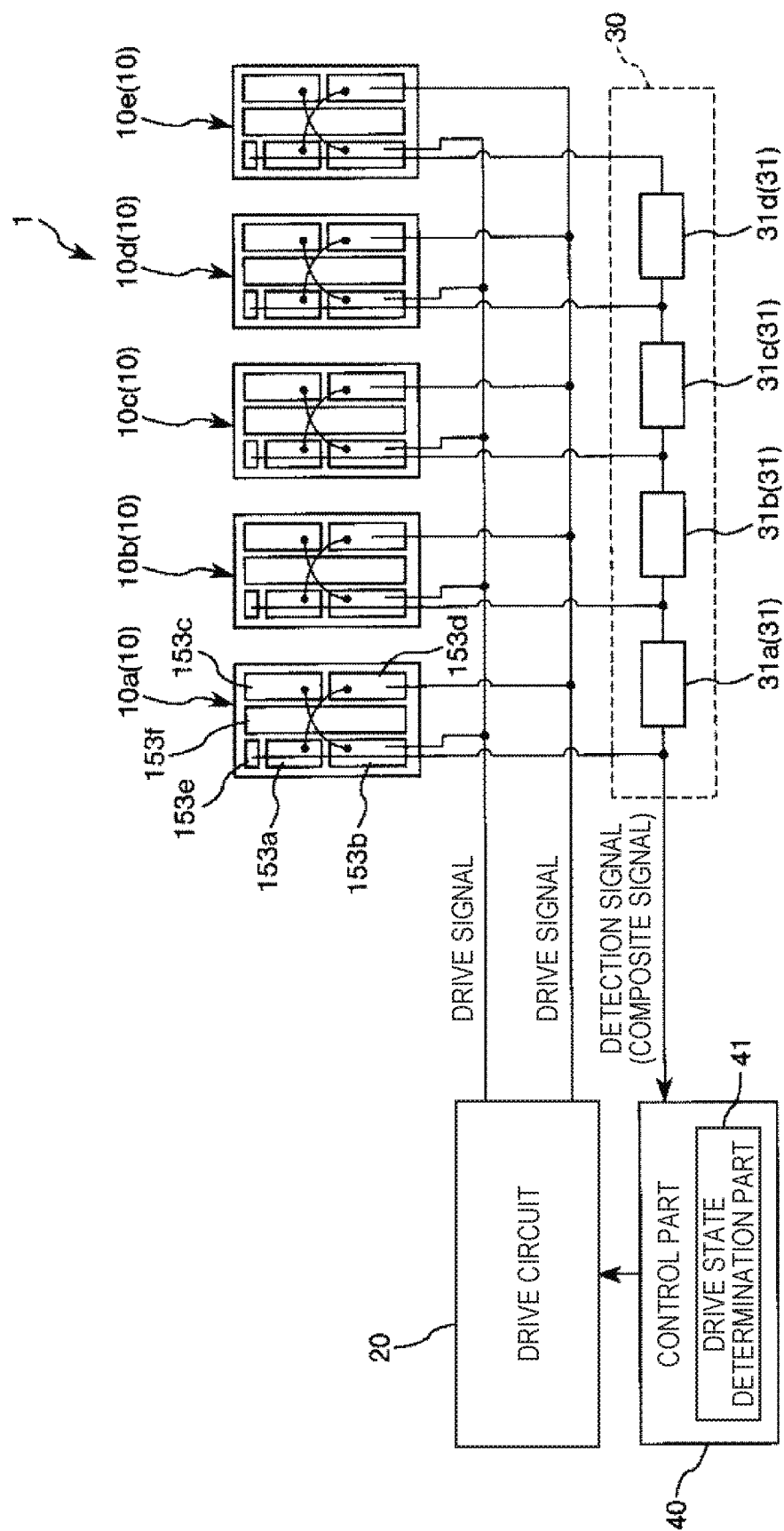
FIG. 1 is a schematic view showing an overall configuration of a piezoelectric actuator according to a first embodiment of the invention.
Figure 2:
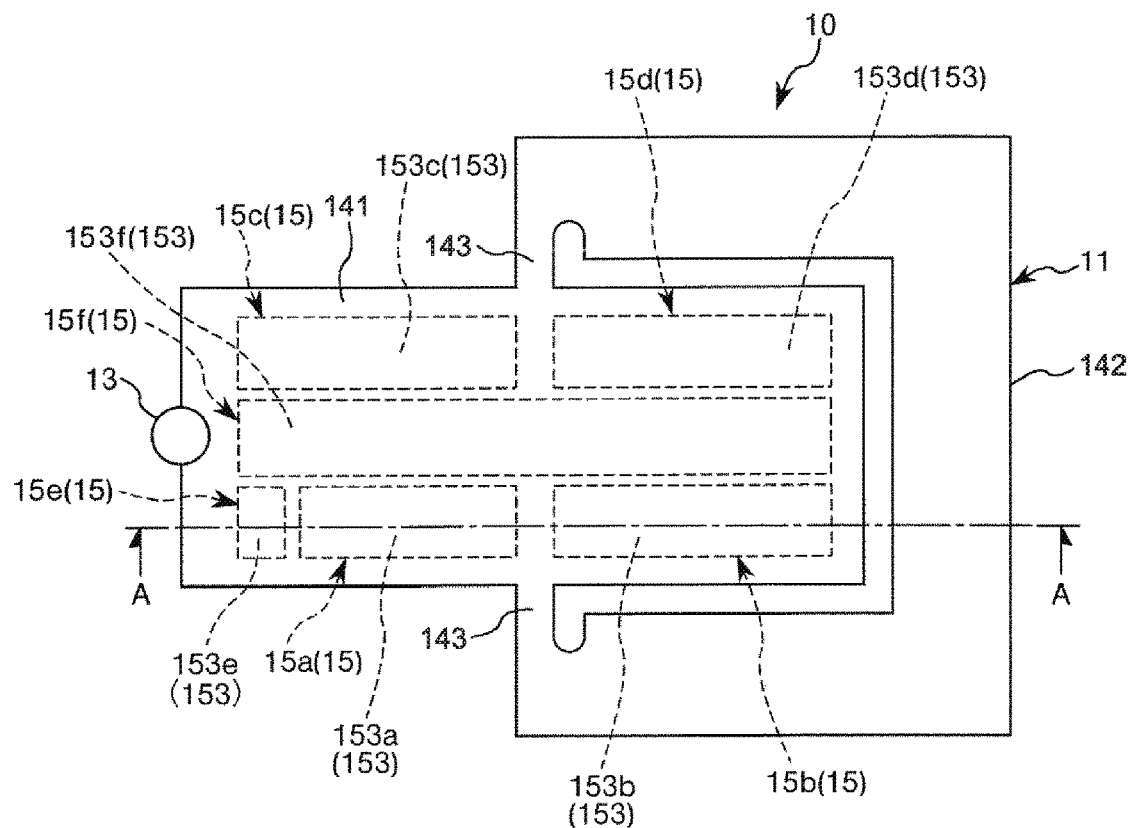
FIG. 2 is a plan view showing a piezoelectric vibrator of the piezoelectric actuator shown in FIG. 1.
Figure 3:
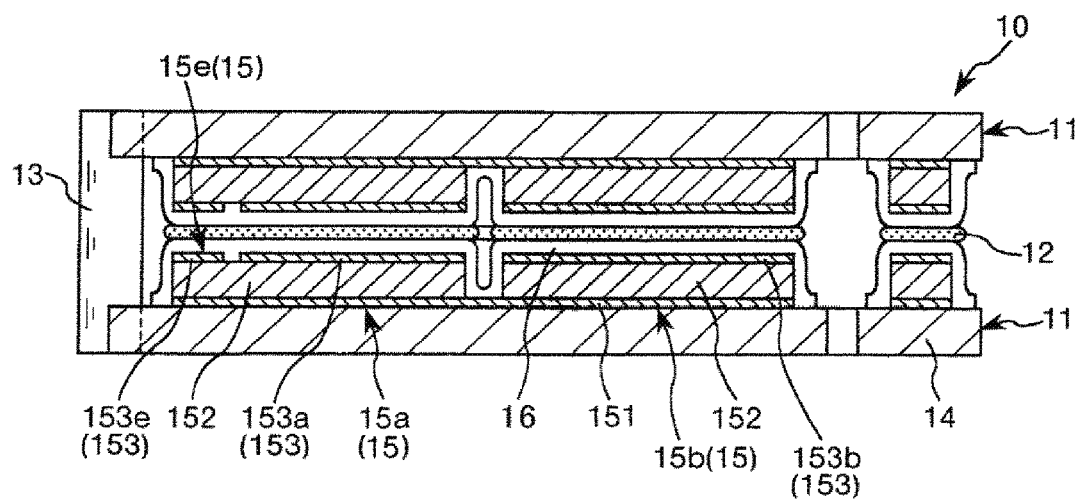
FIG. 3 is a sectional view along A-A in FIG. 2.
Figure 4:
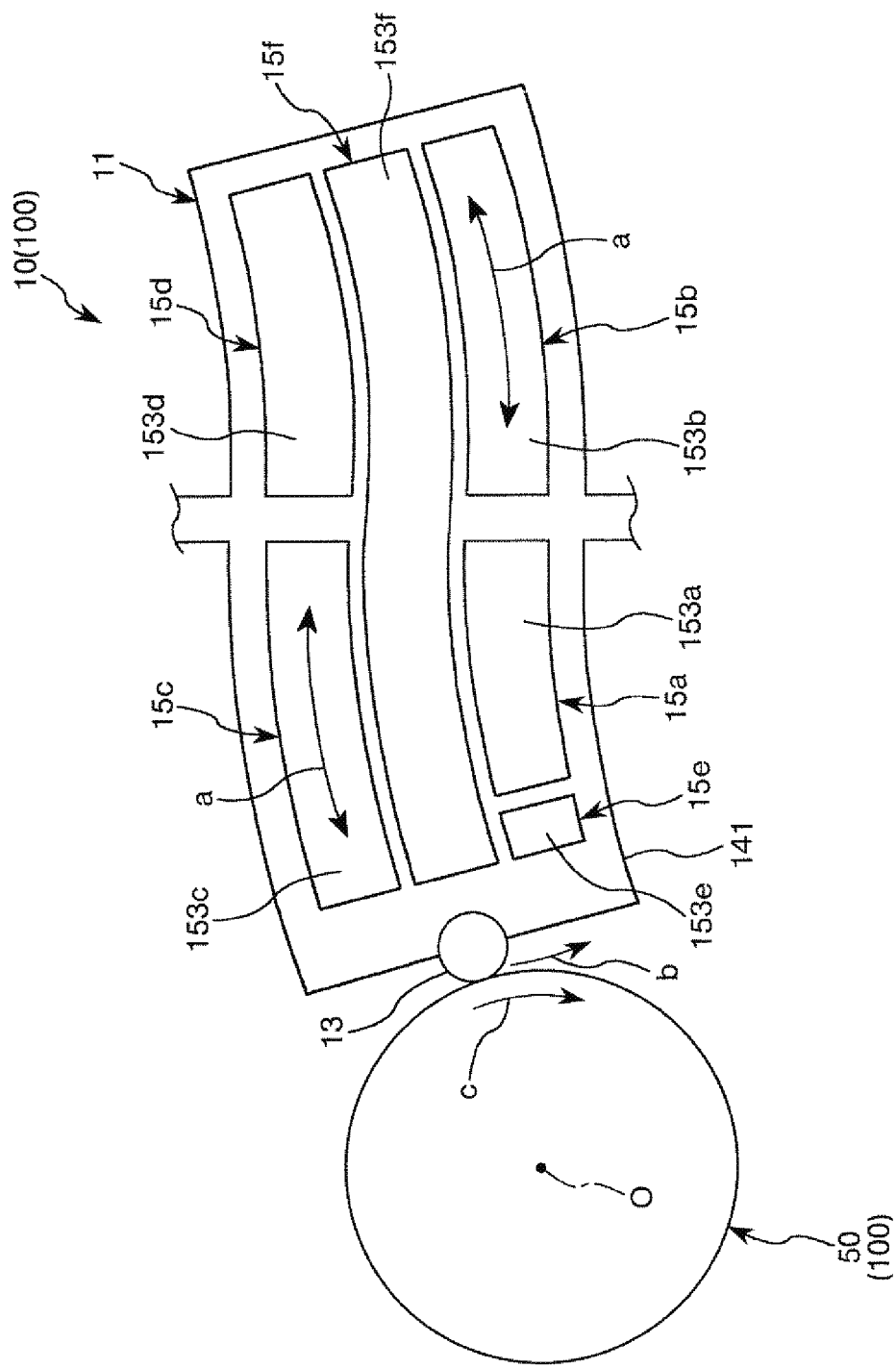
FIG. 4 is a diagram for explanation of motion of the piezoelectric vibrator shown in FIG. 2.

FIG. 1 is a schematic view showing an overall configuration of a piezoelectric actuator according to the first embodiment of the invention. FIG. 2 is a plan view showing a piezoelectric vibrator of the piezoelectric actuator shown in FIG. 1. FIG. 3 is a sectional view along A-A in FIG. 2. FIG. 4 is a diagram for explanation of motion of the piezoelectric vibrator shown in FIG. 2.

The piezoelectric actuator 1 shown in FIG. 1 includes a plurality of piezoelectric vibrators 10 that generate a drive force to be applied to a driven part (not shown), a drive circuit 20 that drives the plurality of piezoelectric vibrators 10, a signal combining part 30 that combines detection signals from the plurality of piezoelectric vibrators 10, and a control part 40 that controls the drive circuit 20 based on a composite signal from the signal combining unit 30. As below, the respective parts of the piezoelectric actuator 1 will be sequentially explained.

Piezoelectric Vibrators

The plurality of piezoelectric vibrators 10 include five piezoelectric vibrators 10a, 10b, 10c, 10d, 10e having the same configuration as one another. The piezoelectric vibrator 10 shown in FIG. 2 has two piezoelectric element units 11, an adhesive layer 12 that bonds the two piezoelectric element units 11 to each other, and a convex member 13 provided over the two piezoelectric element units 11 as shown in FIG. 3. Here, the two piezoelectric element units 11 are symmetrically formed with respect to the adhesive layer 12 (vertically symmetrically in FIG. 3) and have the same configuration as each other.

Each of the piezoelectric element units 11 has a substrate 14, a plurality of piezoelectric elements 15 provided on the substrate 14, and a protective layer 16 that covers the plurality of piezoelectric elements 15.

As shown in FIG. 2, the substrate 14 has a drive part 141, a fixing part 142, and a pair of connecting parts 143 that connect the parts. In the embodiment, the drive part 141 has a rectangular shape in a plan view as seen from the thickness direction of the substrate 14 (hereinafter, simply referred to as "plan view"). The fixing part 142 is provided apart from the drive part 141 along an outer periphery of a portion on one end side of the drive part 141 in the longitudinal direction in the plan view. The pair of connecting parts 143 are provided on both sides of the drive part 141 in the width direction (the direction orthogonal to the longitudinal direction). Further, the pair of connecting parts 143 connect the center portion of the drive part 141 in the longitudinal direction and the fixing part 142. The shape, arrangement, etc. of the drive part 141, the fixing part 142, and the pair of connecting parts 143 are not limited to those described above as long as the drive part 141 can desirably deform or vibrate. For example, the fixing part 142 may be separately provided with respect to each connecting part 143. Further, the number, shape, arrangement of the connecting parts 143 are arbitrary.

As the substrate 14, e.g. a silicon substrate may be used. Further, an insulating layer (not shown) is provided on a surface of the substrate 14 on the piezoelectric elements 15 side. The insulating layer is not particularly limited, but, for example, in the case where the silicon substrate is used as the substrate 14, may be formed by thermal oxidation of the surface of the silicon substrate.

The plurality of piezoelectric elements 15 are provided on the drive part 141 of the substrate 14. In the embodiment, the plurality of piezoelectric elements 15 include five drive piezoelectric elements 15a, 15b, 15c, 15d, 15f and one detection piezoelectric element 15e.

The piezoelectric element 15f is provided along the longitudinal direction of the drive part 141 in the center portion of the drive part 141 in the width direction. The piezoelectric elements 15a, 15b are provided on one side in the width direction of the drive part 141 with respect to the piezoelectric element 15f, and the piezoelectric elements 15c, 15d are provided on the other side. The piezoelectric elements 15a, 15b, 15c, 15d are provided in correspondence with the four areas divided along the longitudinal direction and the width direction of the drive part 141. In the embodiment, the piezoelectric elements 15a, 15b are provided on one side of the drive part 141 in the width direction and the piezoelectric elements 15c, 15d are provided on the other side of the drive part 141 in the width direction. Further, the piezoelectric elements 15a, 15c are provided on one side of the drive part 141 in the longitudinal direction and the piezoelectric elements 15b, 15d are provided on the other side of the drive part 141 in the longitudinal direction. The piezoelectric element 15e is provided on the opposite side to the piezoelectric element 15b with respect to the piezoelectric element 15a on one side of the drive part 141 in the width direction. The arrangement of the piezoelectric element 15e is not limited to that illustrated.

Thus arranged piezoelectric elements 15a, 15b, 15c, 15d, 15e, 15f respectively have a first electrode 151 provided on the substrate 14, piezoelectric materials 152 provided on the first electrodes 151, and second electrodes 153 provided on the piezoelectric materials 152.

The first electrode 151 is a common electrode provided in common with the piezoelectric elements 15a, 15b, 15c, 15d, 15e, 15f. On the other hand, the second electrodes 153 are individual electrodes individually provided with respect to each of the piezoelectric elements 15a, 15b, 15c, 15d, 15e, 15f. In the embodiment, the piezoelectric materials 152 are individually provided with respect to each of the piezoelectric elements 15a, 15b, 15c, 15d, 15f and in common with the piezoelectric elements 15a, 15e. Note that the piezoelectric materials 152 may be individually provided with respect to each of the piezoelectric elements 15a, 15e, or integrally provided in common with the piezoelectric elements 15a, 15b, 15c, 15d, 15e, 15f.

Here, the plurality of second electrodes 153 include the second electrode 153a provided in correspondence with the piezoelectric element 15a, the second electrode 153b provided in correspondence with the piezoelectric element 15b, the second electrode 153c provided in correspondence with the piezoelectric element 15c, the second electrode 153d provided in correspondence with the piezoelectric element 15d, the second electrode 153e provided in correspondence with the piezoelectric element 15e, and the second electrode 153f provided in correspondence with the piezoelectric element 15f.

The second electrode 153a and the second electrode 153d are electrically connected via a wire (not shown). Similarly, the second electrode 153b and the second electrode 153c are electrically connected via a wire (not shown). Further, insulating films such as SiO$_2$ films (not shown) are provided on the second electrodes 153, between the two wires, and elsewhere as appropriate. The first electrode 151 is grounded (connected to the ground potential) via a wire (not shown). The first electrodes 151, the second electrodes 153a or the second electrodes 153d, and the second electrodes 153b or the second electrodes 153c, and the second electrodes 153f of the two piezoelectric element units 11 are respectively electrically connected via wires (not shown).

As the respective constituent materials of the first electrode 151 and the second electrodes 153, e.g. a metal material such as aluminum (Al), nickel (Ni), gold (Au), platinum (Pt), iridium (Ir), or copper (Cu) is used. Further, the first electrode 151 and the second electrodes 153 may be respectively formed by sputtering.

The piezoelectric materials 152 are adapted to expand and contract in the directions along the longitudinal direction of the drive part 141 by application of an electric field in the directions along the thickness direction of the drive part 141. As the constituent material of the piezoelectric materials 152, e.g. piezoelectric ceramics such as lead zirconate titanate (PZT), barium titanate, lead titanate, potassium niobate, lithium niobate, lithium tantalate, sodium tungstate, zinc oxide, barium strontium titanate (BST), strontium bismuth tantalate (SBT), lead metaniobate, or lead scandium niobate may be used. The piezoelectric materials 152 of the piezoelectric ceramics may be formed from a balk material or formed using a sol-gel method, for example. As the constituent material of the piezoelectric materials 152, polyvinylidene fluoride, quartz crystal, or the like may be used.

On the plurality of piezoelectric elements 15a, 15b, 15c, 15d, 15e having the above described configurations, the protective layer 16 is provided to collectively cover the elements. As the constituent material of the protective layer 16, e.g. silicone resin, epoxy resin, polyimide resin, or the like may be used. The protective layer 16 may be formed using e.g. a spin coating method.

Further, the stacked structure including the above described first electrode 151, the piezoelectric material 152, the second electrode 153, and the protective layer 16 are also provided on the fixing part 142 of the substrate 14. Thereby, the two piezoelectric element units 11 may be stably bonded via the adhesive layer 12.

The protective layers 16 having the above described configurations of the two piezoelectric element units 11 are bonded via the adhesive layer 12. The adhesive layer 12 includes e.g. epoxy resin.

The convex member 13 is fixed to the end portions of the drive parts 141 of the two piezoelectric element units 11 on the opposite side to the fixing parts 142 using e.g. an adhesive agent. In the embodiment, the convex member 13 has a cylindrical shape and is provided to partially project from the drive parts 141. As the constituent material of the convex member 13, a material having superior resistance to wear is preferable including e.g. ceramics. The shape of the convex member 13 is not limited to the cylindrical shape as long as the member can transmit the drive force to the driven part.

Drive Circuit

As shown in FIG. 1, the drive circuit 20 is electrically connected to the second electrodes 153b, 153d of the respective five piezoelectric vibrators 10. The drive circuit 20 has a function of respectively inputting voltage signals having periodically changing voltage values as drive signals to the second electrodes 153b, 153d and driving the piezoelectric elements 15a, 15b, 15c, 15d. Further, though not illustrated, the drive circuit 20 is electrically connected to the second electrodes 153f of the respective five piezoelectric vibrators 10. The drive circuit 20 has a function of inputting voltage signals having periodically changing voltage values as drive signals to the second electrodes 153f and driving the piezoelectric elements 15f. The drive circuit 20 has a drive voltage generation circuit (not shown) that outputs the voltage signals having periodically changing voltage values.

When the drive signal having the periodically changing voltage value is input to the second electrode 153b, the piezoelectric elements 15b, 15c respectively repeat expansion and contraction in directions shown by arrows a in FIG. 4. Thereby, the convex member 13 provided in one end portion of the drive part 141 in the longitudinal direction reciprocates (vibrates) in a direction shown by an arrow b in FIG. 4 with flexural vibration of the drive part 141. The drive force of the convex member 13 vibrating as described above is transmitted to a rotor 50 as the driven part, and thereby, the rotor 50 may be rotated in a direction shown by an arrow c in FIG. 4 about a rotation shaft O thereof. Concurrently, the drive signal synchronized with the piezoelectric elements 15b, 15c is input to the piezoelectric element 15f, and thereby, the drive force provided from the convex member 13 to the rotor 50 may be increased and the track of the convex member 13 may be controlled. Note that, even when the drive signal having the periodically changing voltage value is input to the second electrode 153d, similarly, the convex member 13 may be reciprocated (vibrated) in the direction shown by the arrow b in FIG. 4 by driving of the piezoelectric elements 15a, 15d. In this case, the drive signal may be input to the second electrode 153b. In this regard, for example, the phase of the drive signal may be shifted by 180 degrees with respect to the phase of the drive signal input to the second electrode 153d.

Here, the configuration including the piezoelectric actuator 1 and the rotor 50 forms a piezoelectric motor 100. According to the piezoelectric motor 100 including the piezoelectric actuator 1, as will be described later in detail, the failed piezoelectric element 15 of the piezoelectric vibrator 10 of the piezoelectric elements 15 of the plurality of piezoelectric vibrators 10 of the piezoelectric actuator 1 may be specified with simplified wiring of the piezoelectric actuator 1.

In the respective piezoelectric vibrators 10, by the above described driving (vibration), detection signals are output from the second electrodes 153e with the driving by the piezoelectric effect.

Signal Combining Part

As shown in FIG. 1, the signal combining part 30 is electrically connected to the second electrodes 153e of the respective five piezoelectric vibrators 10. The signal combining part 30 has a function of combining the detection signals generated with the driving of the piezoelectric elements 15 of the plurality of piezoelectric vibrators 10 and outputting a composite signal. Particularly, the signal combining part 30 outputs a composite signal by combination of the detection signals from the plurality of piezoelectric vibrators 10 with phase shifts from one another.

The signal combining part 30 has a plurality of delay circuits 31. The plurality of delay circuits 31 include a delay circuit 31d to which the detection signal from the piezoelectric vibrator 10e is input, a delay circuit 31c to which the detection signal from the piezoelectric vibrator 10d and the detection signal from the delay circuit 31d are input, a delay circuit 31b to which the detection signal from the piezoelectric vibrator 10c and the detection signal from the delay circuit 31c are input, and a delay circuit 31a to which the detection signal from the piezoelectric vibrator 10b and the detection signal from the delay circuit 31b are input. As described above, the signal combining part 30 has the four delay circuits 31a, 31b, 31c, 31d. Here, letting the number of piezoelectric vibrators 10 be n (n is an integer equal to or larger than two), the number of delay circuits 31 is (n−1). Note that the piezoelectric elements 15a, 15b, 15c, 15d, 15e of each piezoelectric vibrator 10 output a single detection signal, and may be regarded as single "piezoelectric element 15". That is, in the embodiment, the number of piezoelectric elements 15 that output the detection signals may be regarded as n and, in the example shown in FIG. 1, five.

The delay circuits 31a, 31b, 31c, 31d respectively delay and output the input detection signals or composite signals by lengths of time according to set values. The set values of the delay circuits 31a, 31b, 31c, 31d are set to be equal to one another. In other words, equal amounts of delay (delay times) to one another are set for the delay circuits 31a, 31b, 31c, 31d. The amounts of delay are determined according to the frequencies of the drive signals. As described above, the drive signal is the voltage signal having the periodically changing voltage value, and the detection signal output with the driving of the piezoelectric element 15 is also the voltage signal periodically changing in synchronization with the drive signal. Accordingly, the set values of the delay circuits 31a, 31b, 31c, 31d may be set so that the detection signals may be delayed by desired phase based on the frequencies of the drive signals.

In the embodiment, the amounts of delay of the delay circuits 31a, 31b, 31c, 31d are respectively $2\pi/5$. In other words, the delay circuits 31a, 31b, 31c, 31d respectively delay and output the input detection signals or the detection signal components contained in the composite signals by the phase of $2\pi/5$. Here, letting the number of piezoelectric elements outputting the detection signals, i.e., the number of piezoelectric vibrators 10 be n (n is an integer equal to or larger than two), the amounts of delay of the respective delay circuits 31 are $2\pi/n$. Note that the amounts of delay (delay times) of the delay circuits 31a, 31b, 31c, 31d may be fixed or variable according to the frequencies of the drive signals.

The delay circuits 31a, 31b, 31c, 31d may be respectively formed using e.g. RC circuits having resistors and capacitors. Or, depending on the lengths, resistance values (inductances), or the like of the wires for the detection signals from the piezoelectric vibrators 10, the delay circuits 31a, 31b, 31c, 31d may be formed using the wires. In the point of view, when the amounts of delay of the delay circuits 31 are set as described above, it is also preferable to consider the resistance values of the wires. Note that "amounts of delay of delay circuits 31a, 31b, 31c, 31d" include amounts of delay of signals in the wires for inputting the detection signal or composite signals to the delay circuits and the amounts of delay of signals in the wires for outputting the composite signals from the delay circuits.

Control Part

The control part 40 shown in FIG. 1 has a function of controlling the drive circuit 20 based on the composite signal from the signal combining part 30. Particularly, the control part 40 has a drive state determination part 41 that determines drive states of the respective piezoelectric elements 15 of the plurality of piezoelectric vibrators 10 based on the composite signal from the signal combining part 30.

Determination of Drive States of Piezoelectric Elements

As below, the determination of the drive states of the piezoelectric elements 15 of the piezoelectric vibrators 10 will be explained with reference to FIGS. 5 to 7.

Figure 5:
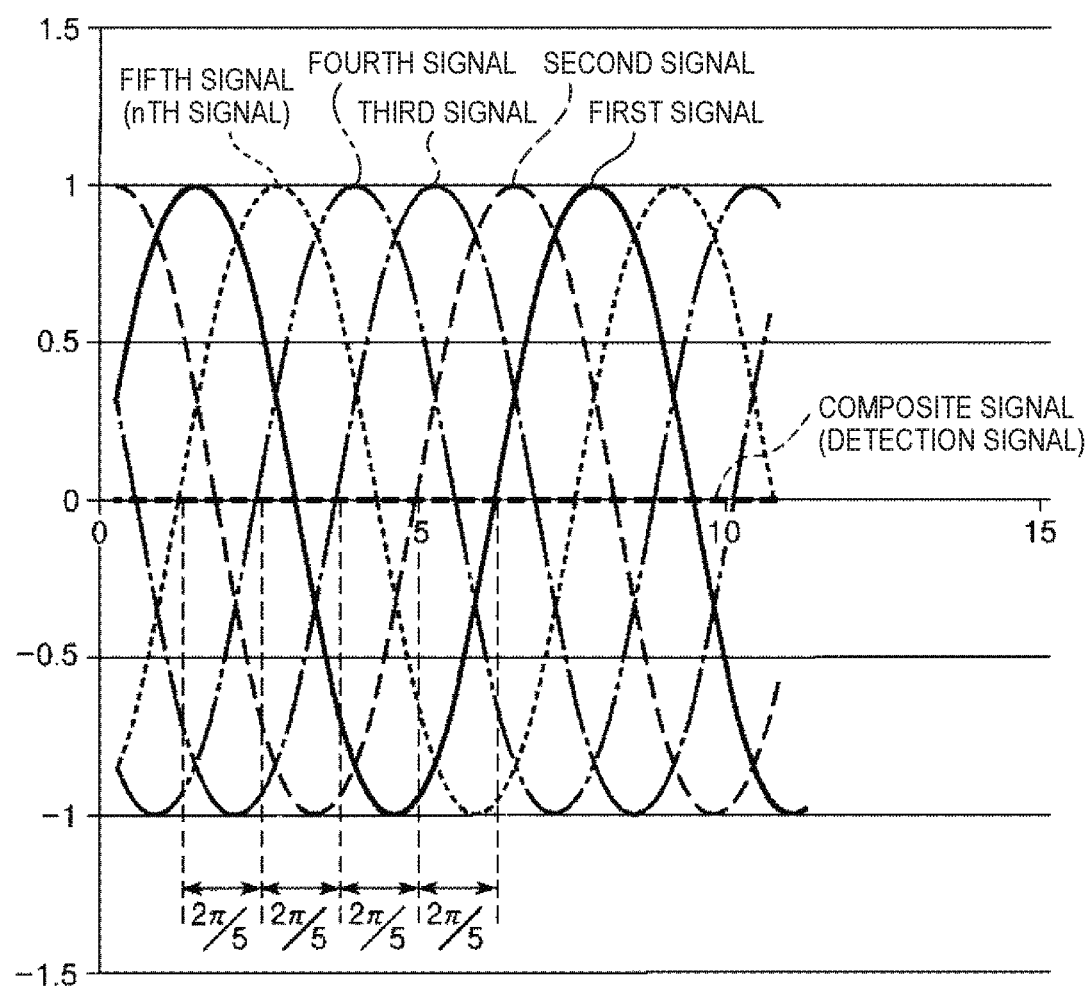
FIG. 5 is a graph showing waveforms of signals from respective piezoelectric elements of the piezoelectric actuator shown in FIG. 1 at a normal time and a composite signal by combination of the signals.

FIG. 5 is a graph showing waveforms of signals from the respective piezoelectric elements of the piezoelectric actuator shown in FIG. 1 at a normal time and a composite signal by combination of the signals.

The detection signals from the piezoelectric vibrators 10a, 10b, 10c, 10d, 10e are output with the driving of the piezoelectric elements 15 of the piezoelectric vibrators 10a, 10b, 10c, 10d, 10e driven by the same drive signal. Therefore, the detection signals are output from the piezoelectric vibrators 10a, 10b, 10c, 10d, 10e basically in phase with one another.

Here, the detection signal from the piezoelectric vibrator 10a is "first signal" and the piezoelectric elements 15 of the piezoelectric vibrator 10a is "first piezoelectric element" that outputs the first signal with driving. The detection signal from the piezoelectric vibrator 10b is "second signal" and the piezoelectric element 15 of the piezoelectric vibrator 10b is "second piezoelectric element" that outputs the second signal with driving. The detection signal from the piezoelectric vibrator 10c is "third signal" and the piezoelectric element 15 of the piezoelectric vibrator 10c is "third piezoelectric element" that outputs the third signal with driving. The detection signal from the piezoelectric vibrator 10d is "fourth signal" and the piezoelectric element 15 of the piezoelectric vibrator 10d is "fourth piezoelectric element" that outputs the fourth signal with driving. The detection signal from the piezoelectric vibrator 10e is "fifth signal" and the piezoelectric element 15 of the piezoelectric vibrator 10e is "fifth piezoelectric element" that outputs the fifth signal with driving. The first to fifth signals are input to the signal combining part 30. Then, the signal combining part 30 delays the phases of the second to fifth signals and outputs a composite signal by combination of the first to fifth signals.

The detection signal from the piezoelectric vibrator 10e passes the delay circuit 31d, the delay circuit 31c, the delay circuit 31b, and the delay circuit 31a in this order. In this regard, the phase of the detection signal from the piezoelectric vibrator 10e is delayed by $2\pi/5$ in each of the delay circuits 31a, 31b, 31c, 31d. Therefore, the phase of the detection signal from the piezoelectric vibrator 10e delays by $8\pi/5$ in total by the delay circuits 31a, 31b, 31c, 31d.

The detection signal from the piezoelectric vibrator 10d passes the delay circuit 31c, the delay circuit 31b, and the delay circuit 31a in this order. In this regard, the phase of the detection signal from the piezoelectric vibrator 10d is delayed by $2\pi/5$ in each of the delay circuits 31a, 31b, 31c. Therefore, the phase of the detection signal from the piezoelectric vibrator 10d delays by $6\pi/5$ in total by the delay circuits 31a, 31b, 31c. Further, the detection signal from the piezoelectric vibrator 10d is combined with the signal from the delay circuit 31d, i.e., the detection signal with the phase delay from the piezoelectric vibrator 10e between the delay circuit 31c and the delay circuit 31d and input to the delay circuit 31c as a composite signal.

The detection signal from the piezoelectric vibrator 10c passes the delay circuit 31b and the delay circuit 31a in this order. In this regard, the phase of the detection signal from the piezoelectric vibrator 10c is delayed by $2\pi/5$ in each of the delay circuits 31a, 31b. Therefore, the phase of the detection signal from the piezoelectric vibrator 10c delays by $4\pi/5$ in total by the delay circuits 31a, 31b. Further, the detection signal from the piezoelectric vibrator 10c is combined with the signal from the delay circuit 31c, i.e., a composite signal having the detection signal components with phase delays from the piezoelectric vibrators 10d, 10e between the delay circuit 31b and the delay circuit 31c and input to the delay circuit 31b as a composite signal.

The detection signal from the piezoelectric vibrator 10b passes the delay circuit 31a. In this regard, the phase of the detection signal from the piezoelectric vibrator 10b is delayed by $2\pi/5$ in the delay circuit 31a. Further, the detection signal from the piezoelectric vibrator 10b is combined with the signal from the delay circuit 31b, i.e., a composite signal having the detection signal components with phase delays from the piezoelectric vibrators 10c, 10d, 10e between the delay circuit 31a and the delay circuit 31b and input to the delay circuit 31a as a composite signal.

The detection signal from the piezoelectric vibrator 10a passes none of the delay circuits 31a, 31b, 31c, 31d, and is combined with the signal from the delay circuit 31a, i.e., a composite signal having the detection signal components with phase delays from the piezoelectric vibrators 10b, 10c, 10d, 10e. Then, a composite signal having all of the detection signal components from the piezoelectric vibrators 10a, 10b, 10c, 10d, 10e is output from the signal combining part 30.

Thereby, the phases of the detection signal from the piezoelectric vibrators 10a, 10b, 10c, 10d, 10e are delayed by $2\pi/5$ from each other by the delay circuits 31a, 31b, 31c, 31d as shown in FIG. 5.

The first to fifth signals are combined into a single composite signal in the above described manner. In the case where none of the piezoelectric vibrators 10a, 10b, 10c, 10d, 10e fails, the composite signal has an amplitude of zero as shown in FIG. 5 because the components of the first to fifth signals at equal phase shift intervals of $2\pi/5$ are cancelled out with each other.

On the other hand, when at least one of the piezoelectric vibrators 10a, 10b, 10c, 10d, 10e does not output the detection signal, not all of the first to fifth signals are cancelled out as described above, and the waveform of the composite signal changes. Therefore, the drive state determination part 41 determines the drive states of the respective piezoelectric elements 15 of the plurality of piezoelectric vibrators 10 based on the composite signal from the signal combining part 30. For example, the drive state determination part 41 individually determines whether or not the respective piezoelectric elements 15 of the plurality of piezoelectric vibrators 10 fail due to disconnection or the like based on the composite signal from the signal combining part 30.

Figure 6:
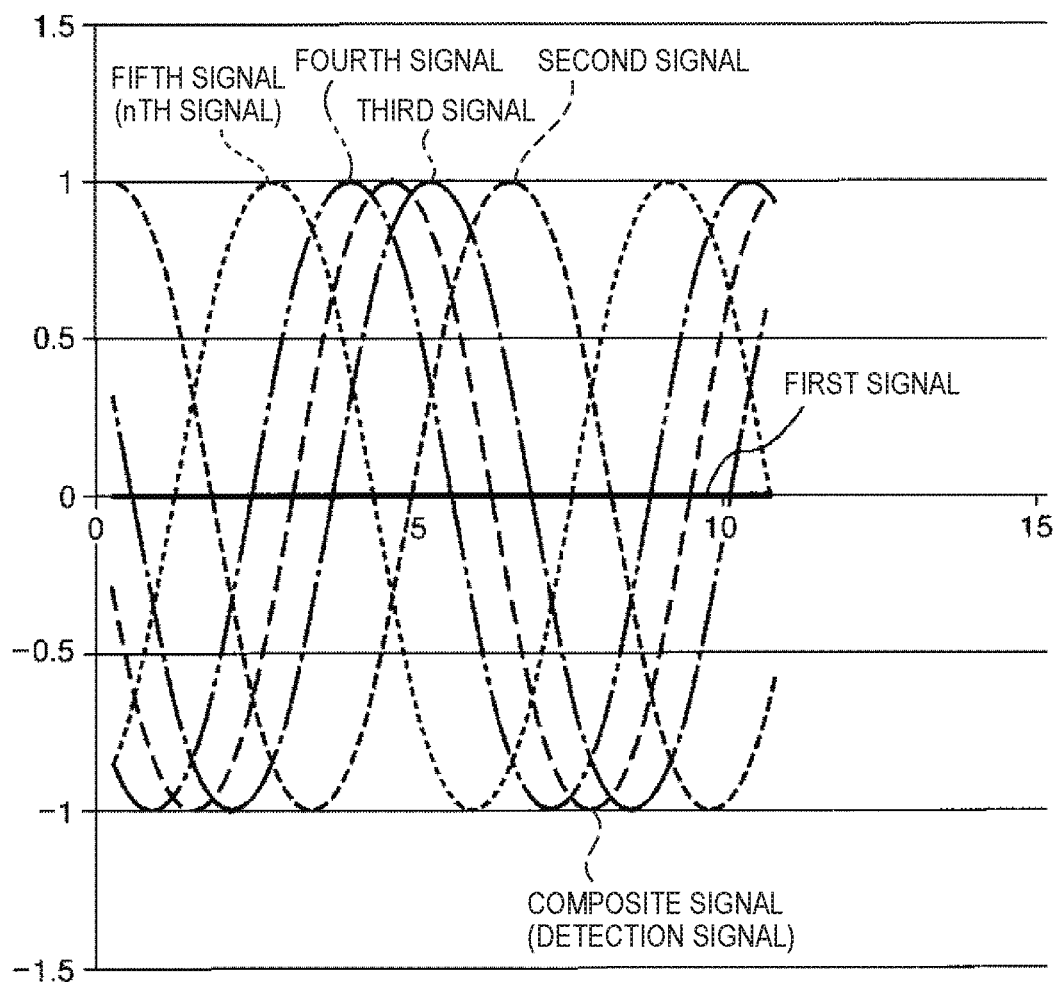
FIG. 6 is a graph showing waveforms of signals from the respective piezoelectric elements of the piezoelectric actuator shown in FIG. 1 when the first piezoelectric element fails and a composite signal by combination of the signals.

FIG. 6 is a graph showing waveforms of signals from the respective piezoelectric elements of the piezoelectric actuator shown in FIG. 1 when the first piezoelectric element fails and a composite signal by combination of the signals.

For example, when the detection signal (first signal) is not output from the piezoelectric vibrator 10a due to a failure or the like of the piezoelectric vibrator 10a, as shown in FIG. 6, the signal component not cancelled out by the first signal appears and the composite signal has a waveform with a phase shift by 180 degrees from the first signal. Therefore, the failure of the piezoelectric vibrator 10a may be determined based on the change in waveform of the composite signal.

Figure 7:
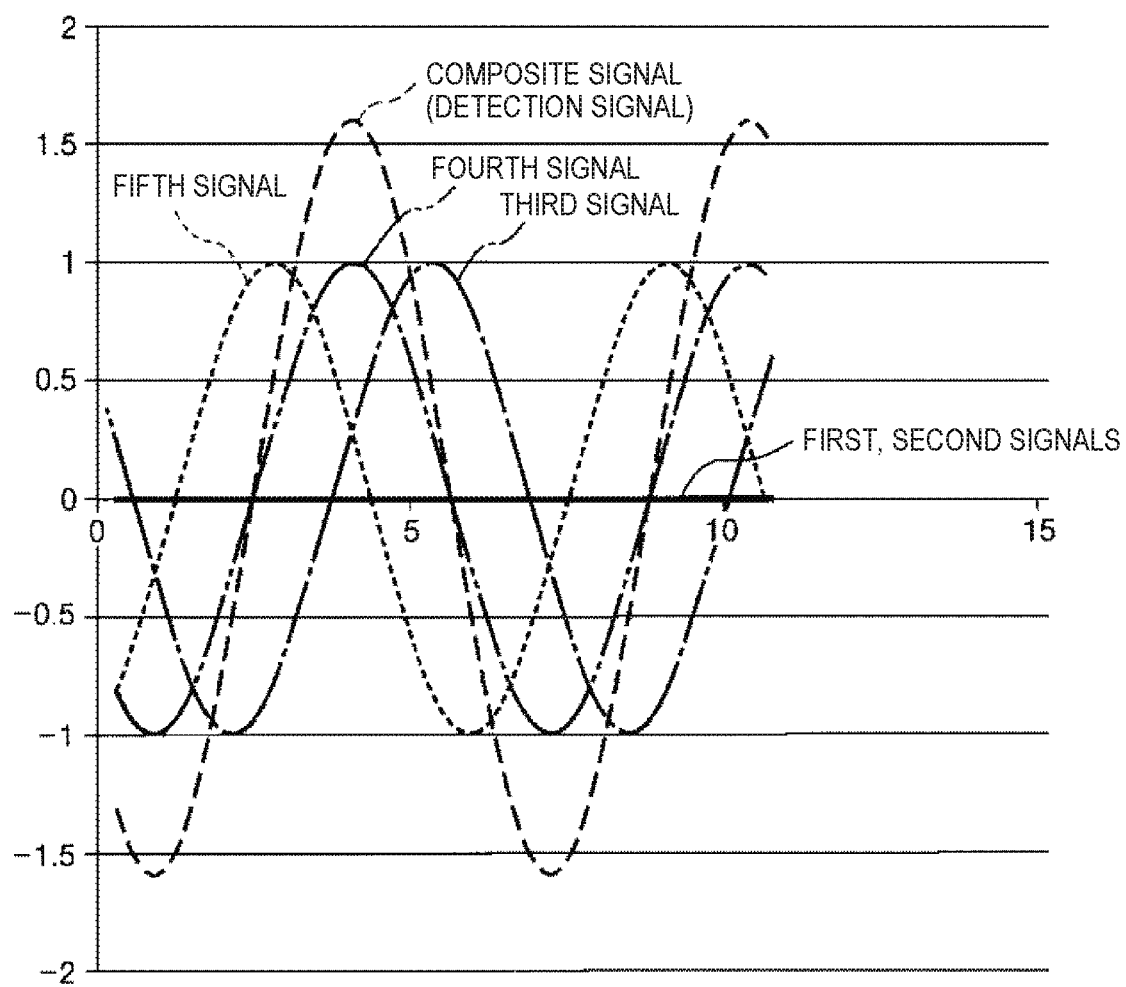
FIG. 7 is a graph showing waveforms of signals from the respective piezoelectric elements of the piezoelectric actuator shown in FIG. 1 when the first, second piezoelectric elements fail and a composite signal by combination of the signals.

FIG. 7 is a graph showing waveforms of signals from the respective piezoelectric elements of the piezoelectric actuator shown in FIG. 1 when the first, second piezoelectric elements fail and a composite signal by combination of the signals.

For example, when the detection signals (first, second signals) are not output from the piezoelectric vibrators 10a, 10b due to failures or the like of the piezoelectric vibrators 10a, 10b, as shown in FIG. 7, the signal components not cancelled out by the first, second signals appear and the composite signal has a waveform formed by combination of a waveform with a phase shift by 180 degrees from the first signal and a waveform with a phase shift by 180 degrees from the second signal. Therefore, the failures of the piezoelectric vibrators 10a, 10b may be determined based on the change in waveform of the composite signal.

In the above described manner, whether or not the respective piezoelectric elements 15 of the piezoelectric vibrators 10a, 10b, 10c, 10d, 10e fail may be determined based on the change in waveform of the composite signal, more specifically, the phase and amplitude appearing in the composite signal.

The determination result may be informed using an informing part (not shown). The informing part includes e.g. a warning light, a display part such as a liquid crystal panel, and a sound generation part such as a speaker. By the information from the informing part, replacement or repair of the failed piezoelectric vibrator may be prompted.

The drive signals input to the piezoelectric vibrators 10a, 10b, 10c, 10d, 10e may be controlled based on the determination result. Thereby, for example, the drive states of all piezoelectric vibrators 10 partially failed may be made closer to the drive states of all piezoelectric vibrators 10 which are not failed.

According to the piezoelectric actuator 1 explained as above, as described above, a composite signal by combination of the detection signals (first to fifth signals) from the piezoelectric elements 15 (first to fifth piezoelectric elements) of the piezoelectric vibrators 10a, 10b, 10c, 10d, 10e with the detection signals (second to fifth signals) with phase delays from the piezoelectric elements 15 of the piezoelectric vibrators 10b, 10c, 10d, 10e is used. Thereby, even when the piezoelectric elements 15 of the piezoelectric vibrators 10a, 10b, 10c, 10d, 10e are driven at the same frequency as one another, in the drive state determination part 41, the changes of the drive states of the piezoelectric elements 15 of the piezoelectric vibrators 10a, 10b, 10c, 10d, 10e may be individually detected based on the changes in waveform of the composite signal. Accordingly, the respective drive states of the piezoelectric elements 15 of the piezoelectric vibrators 10a, 10b, 10c, 10d, 10e may be individually detected by the drive state determination part 41 based on the composite signal without individual input of the respective detection signals from the piezoelectric vibrators 10a, 10b, 10c, 10d, 10e to the drive state determination part 41. Further, the wires from the piezoelectric vibrators 10a, 10b, 10c, 10d, 10e may be integrally grouped to one and connected to the drive state determination part 41. Accordingly, the wires connected to the drive state determination part 41 may be simplified.

Here, as described above, the signal combining part 30 has the plurality of delay circuits 31 having the equal amounts of delay to one another. Thereby, in the case where the number of piezoelectric vibrators 10 is equal to or larger than three as in the embodiment, the composite signal of the signals from the plurality of piezoelectric elements at equal phase shift intervals may be obtained.

Particularly, in the embodiment, as described above, letting the number of piezoelectric vibrators 10 be n (n is an integer equal to or larger than two), the number of delay circuits 31 of the signal combining part 30 is (n−1) and the amounts of delay of the respective delay circuits 31 are $2\pi/n$. Thereby, the composite signal of the signals from the piezoelectric elements 15 of the plurality of piezoelectric vibrators 10 at equal phase shift intervals may be obtained. When part of the piezoelectric elements 15 of the piezoelectric vibrators 10 fail, the waveform of the composite signal changes according to the failed parts. Therefore, the failed piezoelectric elements 15 of the piezoelectric vibrators 10 may be specified based on the waveform change.

Second Embodiment

Next, the second embodiment of the invention will be explained.

Figure 8:
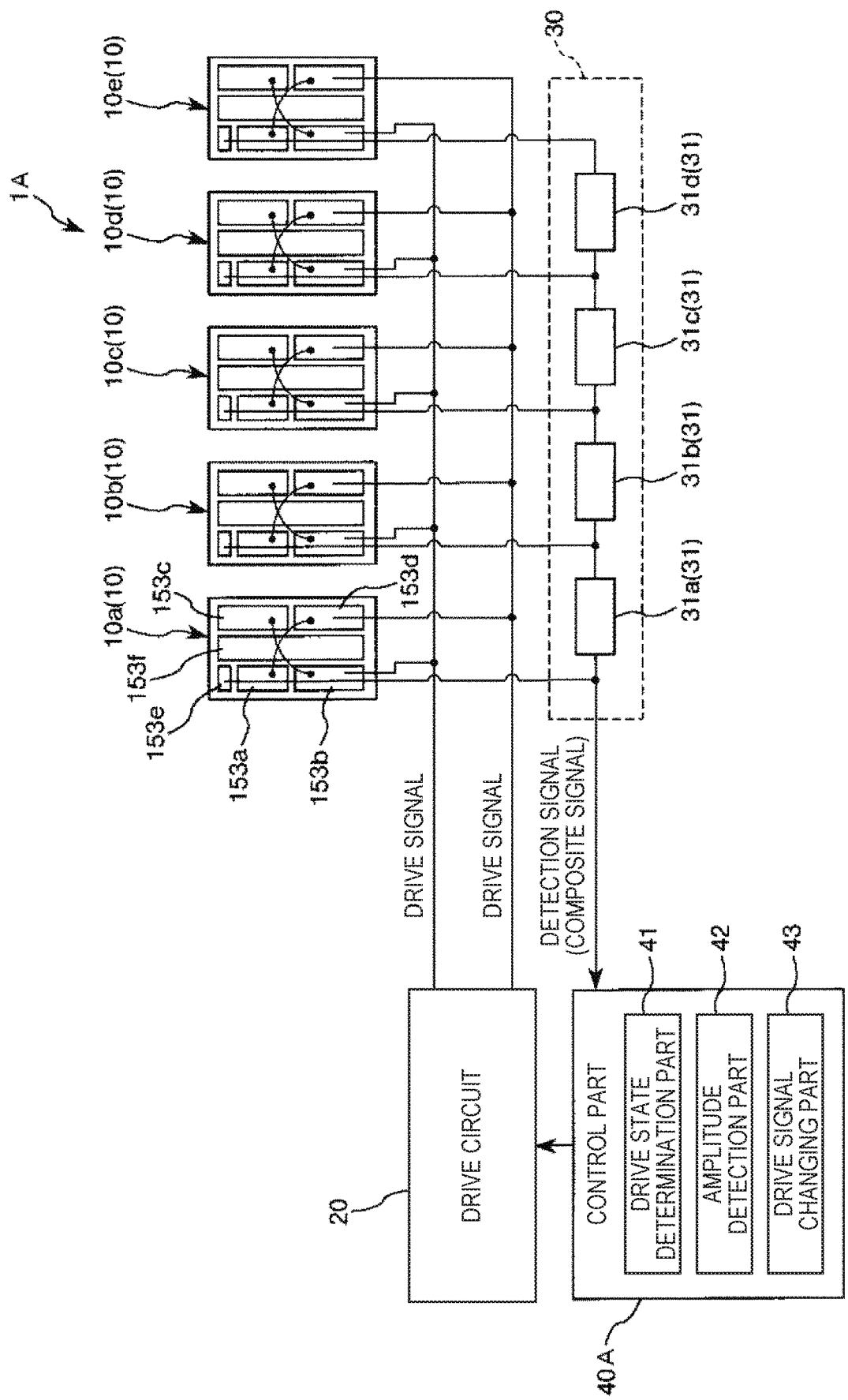
FIG. 8 is a schematic view showing an overall configuration of a piezoelectric actuator according to a second embodiment of the invention.
Figure 9:
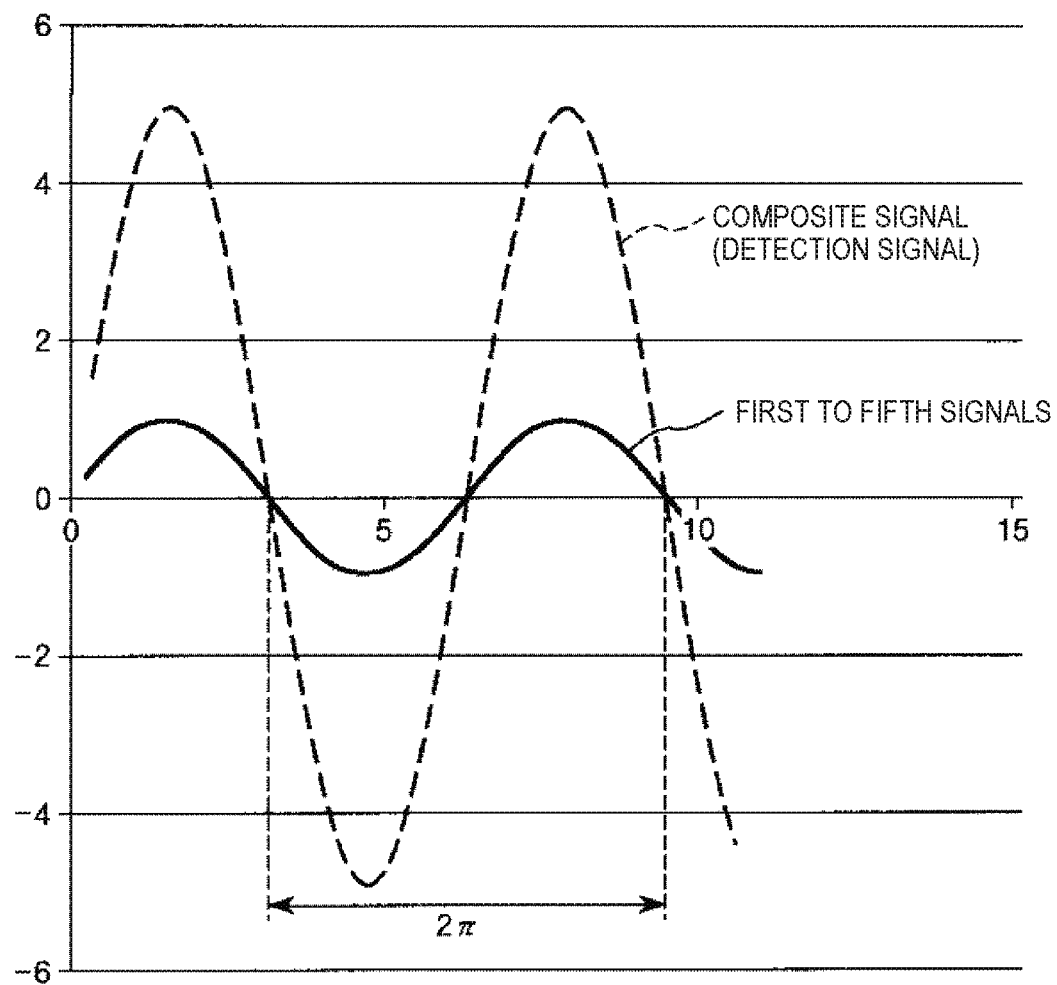
FIG. 9 is a graph showing waveforms of signals from respective piezoelectric elements of the piezoelectric actuator shown in FIG. 8 at a normal time and a composite signal by combination of the signals.

FIG. 8 is a schematic view showing an overall configuration of a piezoelectric actuator according to the second embodiment of the invention. FIG. 9 is a graph showing waveforms of signals from respective piezoelectric elements of the piezoelectric actuator shown in FIG. 8 at a normal time and a composite signal by combination of the signals.

The embodiment is the same as the above described first embodiment except that the determination method of the drive states is different.

In the following explanation, the embodiment will be explained with a focus on the differences from the above described embodiment and the explanation of the same items will be omitted. Further, in FIGS. 8 and 9, the same configurations as those of the above described embodiment have the same signs.

A piezoelectric actuator 1A shown in FIG. 8 includes a control part 40A that controls the drive circuit 20 based on a composite signal from the signal combining part 30. The control part 40A includes an amplitude detection part 42 that detects the amplitude of the composite signal and a drive signal changing part 43 that changes the drive signals input to the piezoelectric elements 15 of the plurality of piezoelectric vibrators 10 based on the detection result of the amplitude detection part 42 in addition to the drive state determination part 41.

In the embodiment, the amounts of delay of the respective delay circuits 31 are $2\pi$. Thereby, as shown in FIG. 9, a composite signal of the detection signals from the piezoelectric elements 15 of the plurality of piezoelectric vibrators 10 in phase may be obtained. When the piezoelectric element 15 of at least one of the piezoelectric vibrators 10 of the plurality of piezoelectric vibrators 10 fails, the amplitude of the composite signal changes according to the number of the failed piezoelectric vibrators 10. More specifically, the amplitude of the composite signal is smaller as the number of the failed piezoelectric vibrators 10 is larger. Therefore, the presence or absence and the number of the failed piezoelectric vibrators 10 may be detected based on the change in amplitude, i.e., the detection result of the amplitude detection part 42. Further, the phases of the detection signals do not change regardless of the presence or absence of the piezoelectric elements 15 of the plurality of piezoelectric vibrators 10. Accordingly, the amplitude detection part 42 is provided, and thereby, the control of the drive signals based on the detection signals may be easily performed in the drive circuit 20.

Here, the signal combining part 30 has the plurality of delay circuits 31 having the equal amounts of delay to one another, and thereby, in the case where the number of piezoelectric vibrators 10 is equal to or larger than three as in the embodiment, the composite signal of the signals from the piezoelectric elements in phase may be obtained.

Then, the drive signal changing part 43 changes the drive signals input to the piezoelectric elements 15 of the plurality of piezoelectric vibrators 10 (first to fifth piezoelectric elements) based on the detection result of the amplitude detection part 42. Thereby, the failed piezoelectric element may be specified based on the composite signal by the change of the drive signals. The change of the drive signals includes e.g. a change of the frequencies of the drive signals and change of the waveforms of the drive signals.

The drive signal changing part 43 changes the frequencies of the drive signals, and thereby, as in the above described first embodiment, a composite signal of the signals from the piezoelectric elements 15 of the plurality of piezoelectric vibrators 10 at equal phase shift intervals may be obtained. More specifically, when the frequencies of the drive signals are changed with the delay times set in the delay circuits 31 fixed, the frequencies of the detection signals are also changed. The frequencies of the detection signals after the change are set to one fifth of the frequencies of the detection signals before the change, and thereby, the amounts of delay of the delay circuits 31 after the change may be set to $2\pi/5$. Therefore, the frequencies of the drive signals are changed after the presence or absence and the number of the failed piezoelectric elements 15 of the piezoelectric vibrators 10 are detected based on the detection result of the amplitude detection part 42, and thereby, the failed piezoelectric elements 15 of the piezoelectric vibrators 10 may be specified based on the composite signal. Note that the composite signal of the signals from the piezoelectric elements 15 of the plurality of piezoelectric vibrators 10 at equal phase shift intervals may be obtained as in the above described embodiment by change of the amounts of delay of the delay circuits 31 with the frequencies of the drive signals fixed.

Further, the drive signal changing part 43 changes the waveforms of the drive signals, and thereby, the signals from the piezoelectric elements 15 of the piezoelectric vibrators 10 except the failed piezoelectric vibrators 10 change. For example, the drive signals with direct-current signals or pulse signals superimposed thereon are input. Then, in the composite signal, the changes appear with shifts of the amounts of delay (delay times) of the delay circuits 31 with respect to each of the piezoelectric vibrators 10. Therefore, the waveforms of the drive signals are changed after the presence or absence and the number of the failed piezoelectric elements 15 of the piezoelectric vibrators 10 are detected based on the detection result of the amplitude detection part 42, and thereby, the piezoelectric elements 15 of the failed piezoelectric vibrators 10 may be specified based on the composite signal (more specifically, the delay time of the waveform change appearing in the composite signal).

Third Embodiment

Next, the third embodiment of the invention will be explained.

Figure 10:
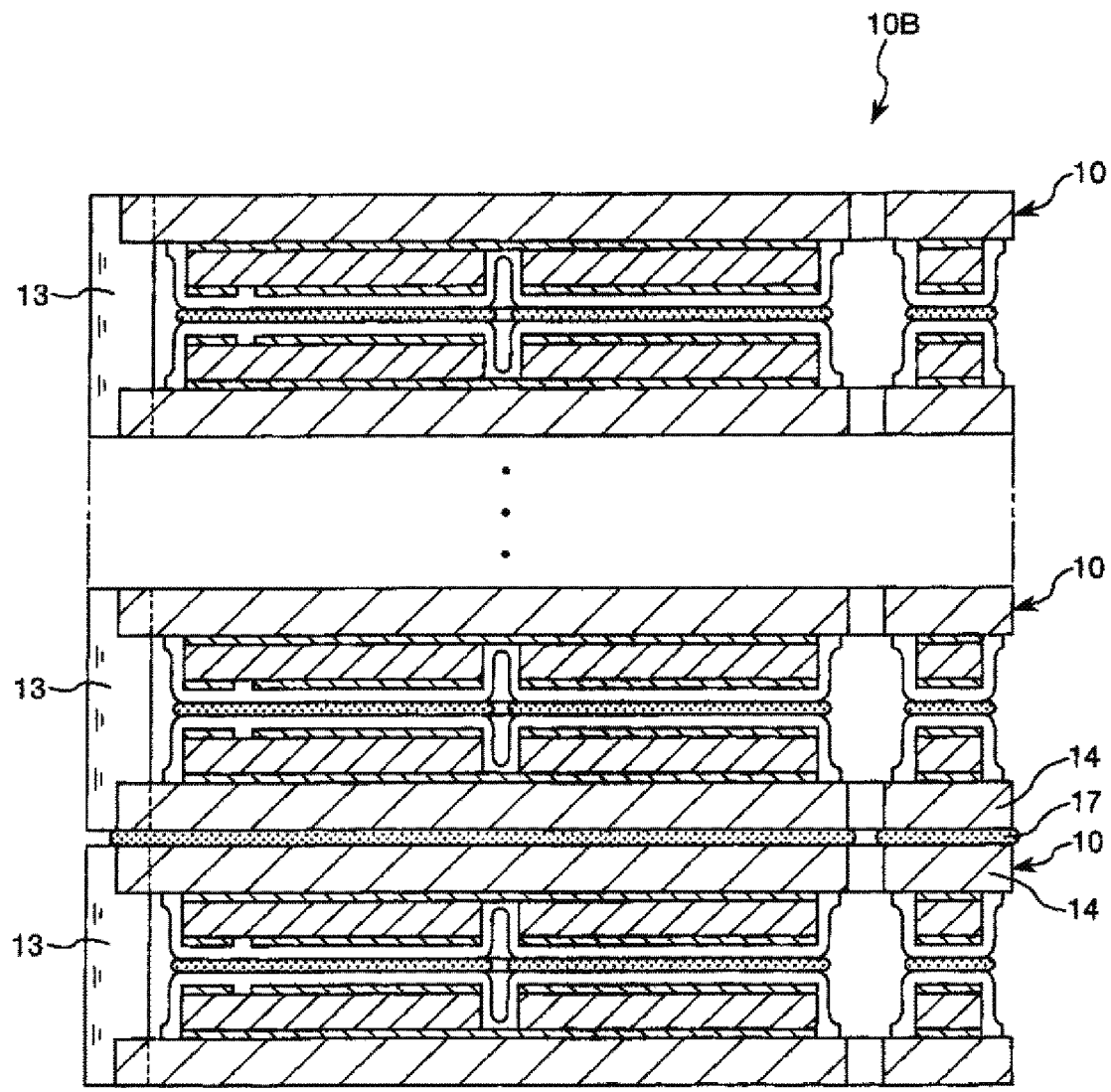
FIG. 10 is a sectional view showing a piezoelectric vibrator of a piezoelectric actuator according to a third embodiment of the invention.

FIG. 10 is a sectional view showing a piezoelectric vibrator of a piezoelectric actuator according to the third embodiment of the invention.

The embodiment is the same as the above described first embodiment except that the configuration of the piezoelectric vibrator is different.

In the following explanation, the embodiment will be explained with a focus on the differences from the above described embodiment and the explanation of the same items will be omitted. Further, in FIG. 10, the same configurations as those of the above described embodiment have the same signs.

As shown in FIG. 10, a piezoelectric vibrator 10B of the piezoelectric actuator of the embodiment has a stacked plurality of piezoelectric vibrators 10. Here, the substrates 14 of the two piezoelectric vibrators 10 adjacent to each other are bonded by an adhesive agent 17. The adhesive agent 17 includes, but is not particularly limited to, e.g. an epoxy-based adhesive agent. The piezoelectric elements 15 of the plurality of piezoelectric vibrators 10 are stacked as described above, and thereby, a large drive force may be transmitted to one part of the driven part. Further, even when the piezoelectric elements 15 of part of the piezoelectric vibrators 10 fail, the failed piezoelectric elements 15 of the piezoelectric vibrators 10 may be driven with driving of the rest of the piezoelectric elements 15 of the piezoelectric vibrators 10.

2. Robot and Hand

Next, embodiments of a robot and a hand according to the invention will be explained.

Figure 11:
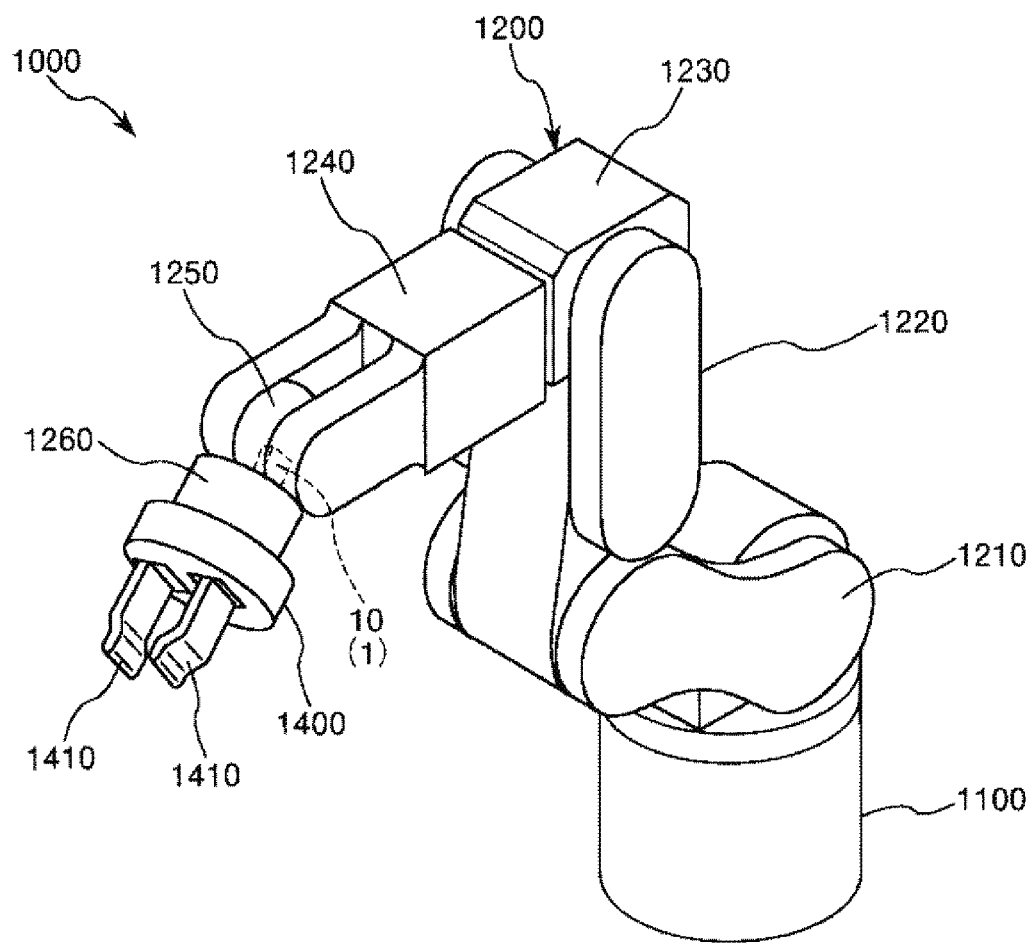
FIG. 11 is a schematic perspective view showing an embodiment of a robot according to the invention.
Figure 12:
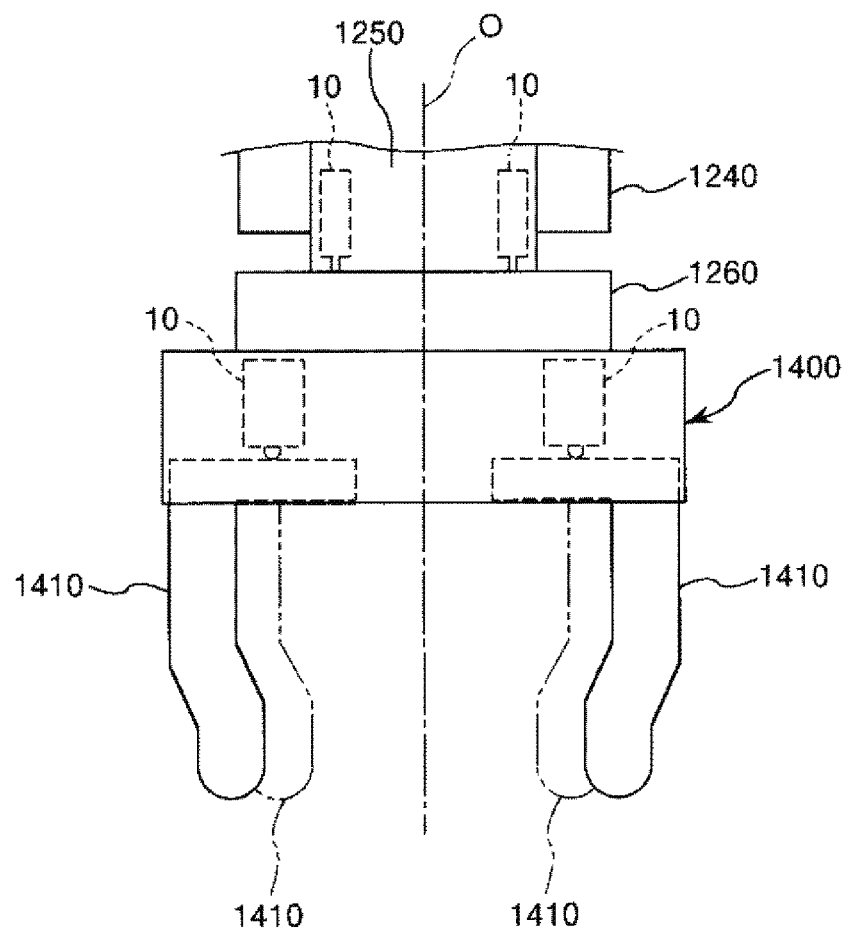
FIG. 12 is a schematic diagram for explanation of a hand of the robot shown in FIG. 11.

FIG. 11 shows a schematic configuration of an embodiment of a robot according to the invention. FIG. 12 is a schematic diagram for explanation of a hand of the robot shown in FIG. 11.

A robot 1000 shown in FIG. 11 performs works of feeding, removing, carrying, assembly, etc. of precision apparatuses and components (objects) forming the apparatuses.

The robot 1000 is a six-axis vertical articulated robot having a base 1100, a robot arm 1200 connected to the base 1100, and a force detector (not shown) and a hand 1400 provided in the distal end part of the robot arm 1200. Further, the robot 1000 has a plurality of drive sources (drive sources including the piezoelectric actuators 1) that generate power to drive the robot arm 1200.

The base 1100 is a part in which the robot 1000 is attached to an arbitrary installation location. The installation location of the base 1100 includes, but is not limited to, e.g. a floor, wall, ceiling, movable platform, etc.

The robot arm 1200 includes a first arm 1210, a second arm 1220, a third arm 1230, a fourth arm 1240, a fifth arm 1250, and a sixth arm 1260, and the arms are sequentially coupled from the proximal end side (base 1100 side) toward the distal end side. The first arm 1210 is connected to the base 1100. On the distal end of the sixth arm 1260, the hand 1400 (end effector) that grasps e.g. various parts or the like is detachably attached. The hand 1400 has two fingers 1410 and may grasp e.g. various parts or the like.

In the fifth arm 1250, a plurality of piezoelectric vibrators 10 are provided as drive sources that drive the sixth arm 1260. Further, drive sources having motors and reducers (not shown) are respectively provided in the base 1100 and the first to fourth arms 1210 to 1240. The respective drive sources are controlled by a control apparatus (not shown).

As shown in FIG. 12, the plurality of piezoelectric vibrators 10 provided in the fifth arm 1250 are arranged side by side in the circumferential direction around a rotation shaft O of the sixth arm 1260 with respect to the fifth arm 1250. The respective piezoelectric vibrators 10 provide a drive force about the rotation shaft O to the end surface of the sixth arm 1260. Thereby, the sixth arm 1260 may be rotated about the rotation shaft O with respect to the fifth arm 1250.

Further, in the hand 1400 as a multi-fingered hand, a plurality of piezoelectric vibrators 10 are provided in correspondence with the respective fingers 1410, and the respective piezoelectric vibrators 10 provide drive forces to the fingers 1410 to move closer to and away from the rotation shaft O. Thereby, the two fingers 1410 may be moved in a direction closer to or away from each other.

According to the above described robot 1000 and hand 1400, the piezoelectric actuators 1 are respectively provided, and the failed piezoelectric elements 15 of the piezoelectric vibrator 10 of the piezoelectric elements 15 of the plurality of piezoelectric vibrators 10 of the piezoelectric actuator 1 may be specified with simplified wiring of the piezoelectric actuator 1.

3. Pump

Next, an embodiment of a pump according to the invention will be explained.

Figure 13:
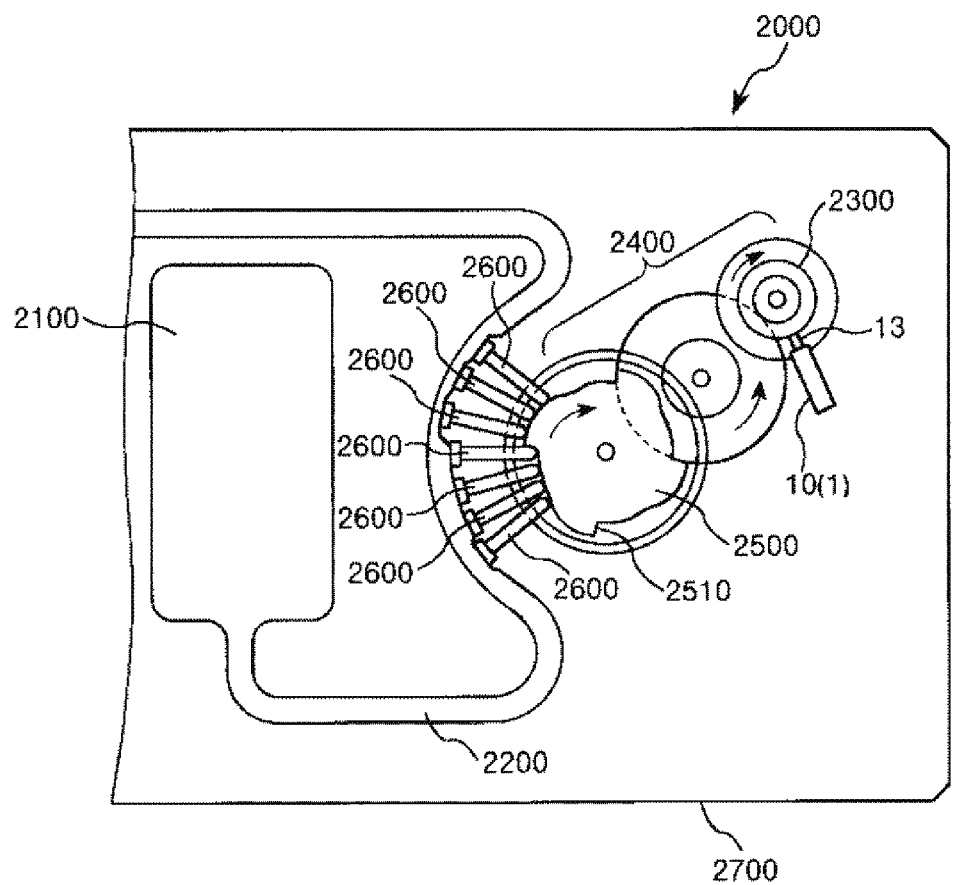
FIG. 13 is a schematic view showing an embodiment of a pump according to the invention.

FIG. 13 is a schematic view showing an embodiment of a pump according to the invention.

A feeding pump 2000 (pump) shown in FIG. 13 has a reservoir 2100, a tube 2200, the piezoelectric actuator 1, a rotor 2300, a reduction transmission mechanism 2400, a cam 2500, and a plurality of fingers 2600, and they are housed within a case 2700. In the reservoir 2100, a liquid to be transported is accumulated. The tube 2200 is a flexible tube having a channel for transporting the liquid from the reservoir 2100. In the plurality of piezoelectric vibrators 10 of the piezoelectric actuator 1, the convex members 13 are in contact with the outer circumferential surface of the rotor 2300 and rotationally drive the rotor 2300. The rotation force of the rotor 2300 is transmitted to the cam 2500 via the reduction transmission mechanism 2400. The plurality of fingers 2600 are provided side by side along the longitudinal direction of the tube 2200 and pressed toward the tube 2200 by projection portions 2510 provided on the outer circumferential surface of the cam 2500 sequentially with the rotation of the cam 2500. Thereby, the plurality of fingers 2600 sequentially block the tube 2000 by pressure from the finger 2600 on the upstream side to the finger 2600 on the downstream side in the transportation direction of the liquid of the tube 2200. Then, the liquid within the tube 2200 is transported from the upstream side to the downstream side in the transportation direction.

According to the feeding pump 2000, a small amount of liquid may be fed with high accuracy and the whole feeding pump 2000 may be downsized. Therefore, the feeding pump 2000 may be preferably used for e.g. a chemical dosing apparatus that doses a chemical such as insulin to a human body or the like.

Particularly, according to the feeding pump 2000, the piezoelectric actuator 1 is provided, and the failed piezoelectric elements of the piezoelectric elements 15 of the plurality of piezoelectric vibrators 10 of the piezoelectric actuator 1 may be specified with simplified wiring of the piezoelectric actuator 1. Accordingly, the feeding pump 2000 is smaller with superior reliability.

As above, the piezoelectric actuator, piezoelectric motor, robot, hand, and pump according to the invention are explained based on the illustrated embodiments, however, the invention is not limited to those. The configurations of the respective parts may be replaced by arbitrary configurations having the same functions. Further, other arbitrary configurations may be added to the invention. Furthermore, the respective embodiments may be appropriately combined.

In the above described embodiments, the case where the drive states of the respective piezoelectric elements are determined using the composite signal by combination of the detection signals from the five piezoelectric elements (the piezoelectric elements of the five piezoelectric vibrators) is explained as an example, however, the number of piezoelectric elements, in other words, the number of detection signals to be combined is not limited to the number in the above described embodiments, but may be from two to four, or six or more.

The entire disclosure of Japanese Patent Application No. 2016-063903, filed Mar. 28, 2016 is expressly incorporated by reference herein.

What is claimed is:

1. A piezoelectric actuator comprising:
    a first piezoelectric element that is configured to output a first signal when being driven;
    a second piezoelectric element that is configured to output a second signal when being driven;
    a signal combining part that is configured to output a composite signal by combination of the second signal with a phase delay and the first signal; and
    a drive state determination part that determines respective drive states of the first piezoelectric element and the second piezoelectric element based on the composite signal.

2. The piezoelectric actuator according to claim 1, wherein the signal combining part has a plurality of delay circuits having equal amounts of delay to one another.

3. The piezoelectric actuator according to claim 1, further comprising n (n is an integer equal to or larger than two) piezoelectric elements including the first piezoelectric element and the second piezoelectric element,
    wherein the signal combining part has (n−1) delay circuits having amounts of delay of $2\pi/n$.

4. The piezoelectric actuator according to claim 1, further comprising an amplitude detection part that is configured to detect an amplitude of the composite signal,
    wherein the signal combining part has a delay circuit having an amount of delay of $2\pi$, and
    the drive state determination part is configured to determine the drive states of the first piezoelectric element and the second piezoelectric element based on a detection result of the amplitude detection part.

5. The piezoelectric actuator according to claim 4, further comprising a drive signal changing part that is configured to change the drive signals input to the first piezoelectric element and the second piezoelectric element based on the detection result of the amplitude detection part.

6. The piezoelectric actuator according to claim 5, wherein the drive signal changing part configured to change frequencies of the drive signals.

7. The piezoelectric actuator according to claim 5, wherein the drive signal changing part configured to change waveforms of the drive signals.

8. The piezoelectric actuator according to claim 1, wherein the first piezoelectric element and the second piezoelectric element are stacked.

9. A piezoelectric motor comprising the piezoelectric actuator according to claim 1.

10. A piezoelectric motor comprising the piezoelectric actuator according to claim 2.

11. A piezoelectric motor comprising the piezoelectric actuator according to claim 3.

12. A piezoelectric motor comprising the piezoelectric actuator according to claim 4.

13. A piezoelectric motor comprising the piezoelectric actuator according to claim 5.

14. A piezoelectric motor comprising the piezoelectric actuator according to claim 6.

15. A piezoelectric motor comprising the piezoelectric actuator according to claim 7.

16. A piezoelectric motor comprising the piezoelectric actuator according to claim 8.

17. A robot comprising the piezoelectric actuator according to claim 1.

18. A hand comprising the piezoelectric actuator according to claim 1.

19. A pump comprising the piezoelectric actuator according to claim 1.

* * * * *